United States Patent [19]
Dicosimo et al.

[11] Patent Number: 5,928,933
[45] Date of Patent: Jul. 27, 1999

[54] **PROCESS FOR THE ENZYMATIC RESOLUTION OF N-(ALKOXYCARBONYL)-4-KETOPROLINE ALKYL ESTERS OR N-(ALKOXYCARBONYL)-4-HYDROXYPROLINE ALKYL ESTERS USING *CANDIDA ANTARCTICA* LIPASE B**

[75] Inventors: Robert Dicosimo, Rockland, Del.; Wonpyo Hong, Lutherville, Md.

[73] Assignee: E. I. du Pont de Nemours & Company, Wilmington, Del.

[21] Appl. No.: 09/105,713

[22] Filed: Jun. 26, 1998

[51] Int. Cl.[6] .............................. C07C 1/04; C12P 13/24
[52] U.S. Cl. ........................ 435/280; 435/107; 435/921
[58] Field of Search .................................... 435/280, 107, 435/921

[56] References Cited

U.S. PATENT DOCUMENTS 3,860,607  1/1975  Leonardo et al. .
5,541,080  7/1996  Sih .

OTHER PUBLICATIONS

Sundram et al., "Chemoenzymatic Synthesis of (2S,3R) – 3–Hydroxyproline from Cyclopentadiene", Tetrahedron Letters 35: 6975–6 (1994).
Greenstein, J.P. et al., Chemistry of the Amino Acids, 3, Chapter 29, John Wiley and Sons: New York, 1961 pp. 2019–2043.
Eguchi et al., *Bull. Chem. Soc. Japan*, 47, 1704–1708, 1986.
Madua et al., *Tetrahedron: Asymmetry*, 7, 825–830, 1996.
Burger et al., *Angew. Chem. Int. Ed. Engl.*, 32, 285–287, 1993.
Mehlfuhrer et al., *J. Chem. Soc. Chem. Commun.*, 11, 1291, 1994.
Seki et al., *Biosci. Biotech. Biochem.*, 59, 1161–1162, 1995.
Papaioannou et al., *Acta Chemica Scandinavica*, 44, 243–251, 1990.
Anderson et al., *J. Org. Chem.*, 61, 7955–7958, 1996.
Leuchs et al., *Chem. Ber.*, 38, 1937, 1905.
Lee et al., *Bull. Chem. Soc. Japan*, 46, 2924, 1973.
Kuhn et al., *Chem. Ber.*, 89, 1423, 1956.
T. Kaneko, *Synth. Prod. Util. Amino Acids*, 13, 123–127, 1974.
Houng et al., *Chirality*, 8, 418–422, 1996.
Chiou et al., *Biotechnology Letters*, 14, 461–464, 1992.
Miyazawa et al., *J. Chem. Soc. Chem. Commun.*, 17, 1214–1215, 1988.
Chen et al., *J. Am. Chem. Soc.*, 104, 7294–7299, 1982.
Patkar et al., *Ind. J. Chem. Sect. B*, 32B, 76–80, 1993.

*Primary Examiner*—Sandra E. Saucier

[57] ABSTRACT

The present invention relates to a process for the enzymatic resolution of racemic mixtures of N-(alkoxycarbonyl)-4-keto-D,L-proline alkyl esters, using *Candida antarctica* lipase fraction B (CALB) as enzyme catalyst to enantioselectively hydrolyze the alkyl ester of one of the two enantiomers present. Separating the unreacted N-(alkoxycarbonyl)-4-keto-D-proline alkyl ester from the N-(alkoxycarbonyl)-4-keto-L-proline, followed by hydrogenation of the keto group of the D-isomer and subsequent hydrolysis of the ester and N-(alkoxy-carbonyl) groups produces cis-4-hydroxy-D-proline in high yield. Diastereomeric mixtures of N-(alkoxycarbonyl)-4-hydroxyproline alkyl esters can also be resolved using CALB to ultimately produce cis-4-hydroxy-D-proline or trans-4-hydroxy-L-proline.

20 Claims, No Drawings

PROCESS FOR THE ENZYMATIC RESOLUTION OF N-(ALKOXYCARBONYL)-4-KETOPROLINE ALKYL ESTERS OR N-(ALKOXYCARBONYL)-4-HYDROXYPROLINE ALKYL ESTERS USING *CANDIDA ANTARCTICA* LIPASE B

FIELD OF THE INVENTION

This invention is in the field of biocatalysis. The present invention relates to a process for the enzymatic resolution of N-(alkoxycarbonyl)-4-ketoproline alkyl esters or N-(alkoxycarbonyl)-4-hydroxyproline alkyl esters. More specifically, this invention pertains to a process for the preparation of cis-4-hydroxy-D-proline and trans-4-hydroxy-L-proline using an enzyme catalyst for enzymatic resolution.

BACKGROUND OF THE INVENTION

The agricultural and pharmaceutical industry seeks production of compounds in high yield with good optical purity. The products of the present invention are useful as precursors for chemicals of high value in these industries. Specifically, cis-4-hydroxy-D-proline (CHDP) and trans-4-hydroxy-L-proline (THLP) are useful for the preparation of agrochemicals and pharmaceuticals.

CHDP is prepared commercially by chemically epimerizing THLP (Greenstein, J. P. and Winitz, M., *Chemistry of the Amino Acids*, vol. 3, chapter 29, John Wiley and Sons: New York (1961)). Required for the synthesis of CHDP, THLP is prepared commercially from hydrolyzed animal gelatin containing approximately 13% of the desired amino acid (U.S. Pat. No. 3,860,607). The overall process to produce CHDP involves expensive chromatographic separation of THLP from the gelatin hydrolysate and produces an excessive amount of waste relative to the amount of CHDP produced.

Alternate methods of preparing CHDP that start from relatively inexpensive starting materials and that produce fewer byproducts and waste than the THLP-based process described above are highly desirable. Several such methods have been reported. A mixture of THLP and CHDP was prepared in six steps and an overall yield of 23% from D-glutamic acid; CHDP was separated from THLP by fractional crystallization (Eguchi et al., *Bull. Chem. Soc. Japan* 47:1704–1708 (1986)). An enantioselective multistep synthesis of either CHDP or cis-4-hydroxy-L-proline (CHLP) from the chiral synthon (6S) and (6R) 6-methyl-4-N-((S)-1-phenylethyl)-1,4-morpholine-2,5-dione has also been reported (Madua et al., *Tetrahedron: Asymmetry* 7:825–830 (1996)).

Preparations of CHLP from L-aspartic acid (Burger et al., *Angew. Chem. Int. Ed. Engl.* 32:285–287 (1993)), from hippuric acid (−)-menthyl ester (Mehlfuhrer et al., *J. Chem. Soc. Chem. Commun.* 11:1291 (1994)), and from THLP have been reported (Seki et al., *Biosci. Biotech. Biochem.* 59:1161–1162 (1995); Papaioannou et al., *Acta Chemica Scandinavica* 44:243–251 (1990); Anderson et al., *J. Org. Chem.* 61:7955–7958 (1996)). Diastereomeric mixtures of hydroxyprolines can be prepared from epichlorohydrin (Leuchs et al., *Chem. Ber.* 38:1937 (1905)), and from allyl bromide (Lee et al., *Bull. Chem. Soc. Japan* 46:2924 (1973)), and racemic mixtures of 4-oxoprolines have been prepared from N-carboethoxyglycine ethyl ester and diethyl fumarate (Kuhn et al., *Chem. Ber.* 89:1423 (1956)). These and similar methods for the production of racemic mixtures of hydroxyprolines have been reviewed by Greenstein and Winitz (In, *Chemistry of the Amino Acids*, vol. 3, chapter 29, John Wiley and Sons: New York (1961)) and T. Kaneko (In, *Synth. Prod. Util. Amino Acids*, "Synthetic Methods for Individual Amino Acids. 13. Hydroxyproline", (Kaneko, T., Izumi, Y., and Chibata, I. eds.) pp. 123–127, Kodansha Ltd.: Tokyo, Japan (1974)).

The use of esterases, lipases and proteases to perform kinetic resolutions of mixtures of enantiomers or diastereomers is well known. The enantioselective hydrolysis of amino acid esters for the resolving racemic amino acids has been reported using a variety of lipases. J.-H. Houng et al., (*Chirality* 8:418–422 (1996)) have described the use of lipases from Rhizopus sp., Pseudomonas sp., and porcine pancreas for the kinetic resolution of N-terminal free amino acids via hydrolysis of their esters, and examined the effect of changes in the ester moiety on the enantioselectivity of the lipases. The observed enantioselectivities were highly dependent on the choice of amino acid, ester moiety and the lipase, where enantiomeric excess of remaining substrates from racemic mixtures ranged from 0 to 100%. A.-I. Chiou et al. (*Biotechnology Letters* 14:461–464 (1992)) have examined the enantioselective hydrolysis of hydrophobic Z-D, L-amino acid methyl esters using lipases from *Aspergillus niger, Geotrichum candidum*, Pseudomonas sp., and *Candida cylindracea*, as well as subtilisin Carlsberg type VIII protease; the observed enantioselectivities were again highly dependent on the choice of amino acid and the lipase, where enantiomeric excess of remaining substrates ranged from 3 to 92%. T. Miyazawa et al. (*J. Chem. Soc. Chem. Commun.* 17:1214–1215 (1988)) have described the use of lipases from Aspergillus niger, Pseudomonas fluorescens, and *Candida cylindracea* for the optical resolution of several unusual N-(benzyloxycarbonyl)-amino acid 2-chloroethyl esters, and noted that the enantioselectivities varied markedly with the enzymes used, and for each enzyme, on the structure of the amino acid; enantiomeric excess of the products ranged from 7 to 95%.

Many additional examples using lipases, as well as esterases and proteases, demonstrate an enantioselective resolution of a mixture of enantiomers (or diastereomers) is highly dependent on not only the choice of enzyme, but also on the chemical structure of the enzyme substrate(s). The optimal choice of enzyme and substrate is therefore not easily predicted, but requires a careful screening of a variety of enzymes while varying the chemical structure of potential substrates.

SUMMARY OF THE INVENTION

The instant invention relates to a process for enzymatically separating racemic or diastereomeric mixtures of compounds. Specifically, this invention concerns separating racemic mixtures of 4-oxo-1,2-pyrrolidinedicarboxylic acid dialkyl esters, herein referred to by the trivial name "N-(alkoxycarbonyl)-4-keto-D,L-proline alkyl esters", of formula I,

I

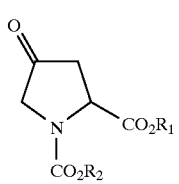

where $R_1$ is selected from the group consisting of unsubstituted or substituted $C_1$–$C_6$ alkyl or alkenyl, and $C_3$–$C_6$ cycloalkyl, and where $R_2$ is independently selected from the group consisting of unsubstituted or substituted $C_1$–$C_6$ alkyl or alkenyl, $C_3$–$C_6$ cycloalkyl, substituted or unsubstituted aryl alkyl, or substituted or unsubstituted heteroaryl alkyl, by enzymatic resolution using *Candida antartica* lipase fraction B (CALB) as an enzyme catalyst to enantioselectively hydrolyze the ester of the corresponding L-isomer of the racemate. After separating the unreacted N-(alkoxycarbonyl)-4-keto-D-proline alkyl ester from the N-(alkoxy-carbonyl)-4-keto-L-proline, the keto-group of the D-isomer is hydrogenated with high enantioselectivity to produce N-(alkoxycarbonyl)-cis-4-hydroxy-D-proline alkyl ester, and the ester and N-(alkoxycarbonyl) groups subsequently hydrolyzed to produce CHDP in high yield.

In a further embodiment, the instant invention concerns separating diastereomeric mixtures. Specifically, this invention concerns separating diastereomeric mixtures of 4-hydroxy-1,2-pyrrolidinedicarboxylic acid dialkyl esters, herein referred to by the trivial name "N-(alkoxycarbonyl)-4-hydroxyproline alkyl esters", of formula II,

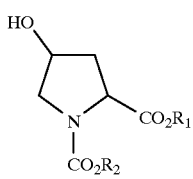

where $R_1$ is selected from the group consisting unsubstituted or substituted $C_1$–$C_6$ alkyl or alkenyl, and $C_3$–$C_6$ cycloalkyl, and where $R_2$ is independently selected from the group consisting of unsubstituted or substituted $C_1$–$C_6$ alkyl or alkenyl, $C_3$–$C_6$ cycloalkyl, substituted or unsubstituted aryl alkyl, or substituted or unsubstituted heteroaryl alkyl, by enzymatic resolution using CALB as enzyme catalyst to enantioselectively hydrolyze the alkyl ester of one of the two diastereomers. The unhydrolyzed N-(alkoxycarbonyl)-4-hydroxyproline alkyl ester is readily separated from the product N-(alkoxycarbonyl)-4-hydroxyproline diastereomer in high yield. In this manner, N-(alkoxycarbonyl)-cis-4-hydroxy-D-proline alkyl ester may be separated from a mixture of two diastereomers, and subsequent hydrolysis of the ester and N-(alkoxycarbonyl) groups of N-(alkoxycarbonyl)-cis-4-hydroxy-D-proline alkyl ester produces CHDP in high yield.

DETAILED DESCRIPTION OF THE INVENTION

The present invention relates to a process for the enzymatically resolving racemic mixtures of N-(alkoxycarbonyl)-4-keto-D,L-proline alkyl esters, using *Candida antartica* lipase fraction B (CALB) as an enzyme catalyst to enantioselectively hydrolyze the alkyl ester of one of the two enantiomers present. Separating unreacted N-(alkoxycarbonyl)-4-keto-D-proline alkyl ester from the N-(alkoxycarbonyl)-4-keto-L-proline, followed by hydrogenation of the keto group of the D-isomer and subsequent hydrolysis of the ester and N-(alkoxycarbonyl) groups produces CHDP in high yield. Diastereomeric mixtures of N-(alkoxycarbonyl)-4-hydroxyproline alkyl esters can also be resolved using CALB to ultimately produce such products as CHDP or THLP.

Additionally, the method of the present invention is preferred for separating diastereomeric mixtures of N-(alkoxycarbonyl)-4-hydroxyproline alkyl esters relative to non-enzymatic methods for separating diastereomers in mixtures of components with similar chemical properties. In such cases, the components are not readily separated by differences in solubilities or by fractional crystallization. This is the case in the present invention for diastereomeric mixtures of N-(alkoxycarbonyl)-cis-4-hydroxy-D,L-proline alkyl esters and for diastereomeric mixtures of N-(alkoxycarbonyl)-trans-4-hydroxy-D,L-proline alkyl esters.

The products of the present invention are useful as precursors for chemicals of high value in the agricultural and pharmaceutical industries. Relative to previously known chemical methods, the claimed invention generates little waste and permits a facile approach to product recovery.

In this disclosure, a number of terms and abbreviations are used. The following definitions are provided.

"Cis-4-hydroxy-D-proline" is abbreviated as CHDP.

"Cis-4-hydroxy-L-proline" is abbreviated as CHLP.

"Trans-4-hydroxy-L-proline" is abbreviated as THLP.

"*Candida antartica* lipase fraction B" is abbreviated as CALB.

"Racemic mixtures of 4-oxo-1,2-pyrrolidinedicarboxylic acid dialkyl esters" are herein referred to by the trivial name N-(alkoxycarbonyl)-4-keto-D,L-proline alkyl esters.

"Enantiomeric excess" is abbreviated as ee.

"Enantioselectivity" is abbreviated as E.

"Diasteriomeric excess" is abbreviated as de.

"N-(methoxycarbonyl)-4-keto-L-proline methyl ester" is abbreviated as KLP(MEMC).

"N-(methoxycarbonyl)-4-keto-D-proline methyl ester" is abbreviated as KDP(MEMC).

"N-(methoxycarbonyl)-4-keto-L-proline" is abbreviated as KLP(MC).

"N-(ethoxycarbonyl)-4-keto-L-proline ethyl ester" is abbreviated as KLP(EEEC).

"N-(ethoxycarbonyl)-4-keto-D-proline ethyl ester" is abbreviated as KDP(EEEC).

"N-(methoxycarbonyl)-cis-4-hydroxy-D-proline methyl ester" is abbreviated as CHDP(MEMC).

"N-(methoxycarbonyl)-cis-4-hydroxy-L-proline methyl ester" is abbreviated as CHLP(MEMC).

"N-(methoxycarbonyl)-trans-4-hydroxy-D-proline methyl ester" is abbreviated as THDP(MEMC).

"N-(methoxycarbonyl)-trans-4-hydroxy-L-proline methyl ester" is abbreviated as THLP(MEMC).

"N-(ethoxycarbonyl)-trans-4-hydroxy-L-proline methyl ester" is abbreviated as THLP(MEMC).

"N-(tert-butoxycarbonyl)-trans-4-hydroxy-L-proline methyl ester" is abbreviated as THLP(MEBOC).

The term "enantiomer" is used to describe one of a pair of molecular entities which are mirror images of each other and non-superimposable.

The term "diasteriomer" is used to describe stereoisomers not related as mirror images. Diasteriomers are characterized by differences in physical properties and by some differences in chemical behavior towards achiral as well as chiral reagents.

The term "enantiomeric excess" is defined for a mixture of (+)- and (−)-enantiomers, with composition given as the mole or weight fraction $F_{(+)}$ and $F_{(-)}$ (where the sum of $F_{(+)}$ and $F_{(-)}=1$) the enantiomeric excess is defined as $|F_{(+)}-F_{(-)}|$ and the percent enantiomeric excess by 100 $|F_{(+)}-F_{(-)}|$.

The term "diastereomeric excess" is defined by analogy with enantiomeric excess, as $D_1-D_2$ [and the percent diastereomeric excess as $100(D_1-D_2)$], where the mole fractions of two diasteriomers in a mixture of the fractional yields of two diastereomers formed in a reaction are $D_1$ and $D_2$ (where the sum of $D_1$ and $D_2=1$). The term is not applicable when more than two diastereomers are present.

As used herein, the term "enantioselectivity" or the symbol "E" refers to the selective capacity of an enzyme to generate from a racemic substrate one enantiomer relative to the other in a product racemic mixture. The enantioselectivity resides in a difference in conversion rates between the enantiomers in question. Reaction products are obtained that are enriched in one of the enantiomers. For practical purposes it generally is desirable for one of the enantiomers to be obtained in large excess. This is achieved by terminating the conversion at a certain degree of conversion. The enantioselectivity is quantitatively expressed by the following formula (U.S. Pat. No. 5,541,080; Chen et al., *J. Am. Chem. Soc.* 104:7294–7299 (1982)):

$$\frac{\ln[(1-c)(1-ee(S))]}{\ln[(1-c)(1+ee(S))]} = E$$

$$c = 1 - \frac{A+B}{A_0-B_0} \quad ee(S) = \frac{B-A}{A+B}$$

wherein:

c is the extent of substrate conversion for the enzyme catalyzed product, ee(S) is the enantiomeric excess of the recovered substrate fraction, and A and B are the two competing enantiomers. The general theory regarding enantioselective conversion described in these publications also applies to the present process.

A. Enzymatic resolution of 4-ketoproline derivatives.

Chemical synthesis of 4-ketoproline derivatives from inexpensive achiral starting materials will typically produce a racemic mixture of two enantiomers. It has been reported that hydrogenation of either D- or L-enantiomer of 4-ketoproline derivatives can produce the corresponding cis-4-hydroxyproline derivatives with high selectivity (Kuhn et al., *Chem. Ber.* 89:1423 (1956)), so an enzymatic resolution of a racemic mixture of D- and L-4-ketoproline derivatives would allow for the hydrogenation of the 4-keto-D-proline derivative to produce CHDP. Chemical or enzymatic racemization of the remaining 4-keto-L-proline derivative to a 50/50 mixture of D- and L-isomers could allow the undesired L-isomer to be recycled back into the resolution step. Alternatively, if the 4-keto-L-proline derivative could be reduced and hydrolyzed to THLP, the THLP is readily converted to CHDP by chemical isomerization.

An enzyme catalyst for the enzymatic resolution of racemic D,L-4-ketoproline derivatives was desired which would hydrolyze the methyl ester of only one of the two enantiomers present in the racemic mixture with a high degree of enantioselectivity (>95% enantiomeric excess (ee) of remaining substrate) at 50% conversion of a racemic mixture, such that the remaining 4-ketoproline derivative mixture would be 97.5% D- and 2.5% of the L-isomer or 97.5% L-isomer and 2.5% of the D-isomer. The calculations of ee and enantioselectivity (E) relative to conversion in enzymatic resolutions of racemic mixtures of chiral compounds have been described in the literature (U.S. Pat. No. 5,541,080). If an enzyme catalyst has a low enantioselectivity for one of the two enantiomers present, an enantiomeric excesses of remaining substrate of at least 95% can only be obtained by running the reaction to conversions considerably in excess of 50% conversion, which results in an undesirable and uneconomical yield loss due to the necessary conversion of significant percentages of both enantiomers.

A racemic mixture of N-(methoxycarbonyl)-4-keto-L-proline methyl ester (KLP(MEMC)) and N-(methoxycarbonyl)-4-keto-D-proline methyl ester (KDP (MEMC)) was prepared by a modification of the method of Kuhn et al., *Chem. Ber.* 89:1423 (1956)). Distillation and recrystallization from acetone produced approximately 99% pure KDP(MEMC)/KLP(MEMC). KDP(MEMC) and KLP (MEMC) were each also individually prepared from CHDP and THLP, respectively, in three steps by esterification with methanol/thionyl chloride, reaction of the resulting methyl ester with methyl chloroformate, and subsequent oxidation of the 4-hydroxy group with sodium periodate/ruthenium trichloride. The racemic N-(ethoxycarbonyl)-4-keto-D,L-proline ethyl esters KDP(EEEC) and KLP(EEEC) were prepared by reacting N-(ethoxycarbonyl)-glycine ethyl ester with maleic acid diethyl ester according to the method described above for racemic KDP(MEMC)/KLP(MEMC).

A racemic mixture of KDP(MEMC) and KLP(MEMC) was screened against forty-four different commercial protease, lipase and esterase enzyme preparations (Example 1), and only one enzyme was found to hydrolyze the methyl ester of the L-isomer of the racemate with high ($\geq$95% ee substrate) enantioselectivity at 50% conversion. Reacting a 0.10M solution of the 1:1 mixture of KDP(MEMC) and KLP(MEMC) in 0.20M succinate (pH 6.0) at 25° C. for 5 h with approximately 1–3 mg/mL of *Candida antartica* lipase fraction B (CALB) produced a 95% ee (substrate) of KDP (MEMC) at 51% conversion. This corresponds to 97.5% of KDP(MEMC) and only 2.5% of KLP(MEMC) remaining at 51% conversion. The calculated enantioselectivity (E) at 51% conversion was E=81. A blank check of the stability of the KDP(MEMC) and KLP(MEMC) derivatives at pH 6.0 under identical reaction conditions without added enzyme indicated that approximately 3% of each isomer was lost in the same 5 h reaction time, which means that the 2.5% loss of the D isomer may have been due solely to a non-enzymatic reaction, and that the enantioselectivity was actually much higher than measured.

The enzymatic hydrolysis reaction of KDP(MEMC) and KLP(MEMC) using CALB (described above) was repeated at pH 5.0 in 0.20M acetate buffer (Example 2), and a 100% ee (substrate) of the D-isomer was obtained at 51% conversion (E=>1000); the reaction rate was approximately 50% of the rate at pH 6.0, and the slight loss of the D-isomer at pH 5.0 was again observed in the absence of added enzyme (95% recovery at pH 5.0 after 24 h with no enzyme). The production of N-(methoxycarbonyl)-4-keto-L-proline (KLP (MC)) as the reaction product was confirmed by the preparation of an authentic sample of KLP(MC), which had an identical $^1$H and $^{13}$C NMR spectra and HPLC retention time as the reaction product.

Several additional ketoproline derivatives were prepared and screened as potential substrates for enzyme-catalyzed resolution. The CALB-catalyzed enzymatic resolution of racemic N-(ethoxycarbonyl)-4-keto-D,L-proline ethyl ester (KLP(EEEC)/KDP(EEEC)) produced a 100% ee (substrate) of KDP(EEBC) at 51% conversion of the racemic mixture. A racemic mixture of N-(2-phenylacetyl)-D,L-4-ketoproline methyl esters could also be separated with relatively high enantioselectivity (E=29) using CALB. Other ketoproline derivatives could not be resolved using the enzyme catalysts which were examined; racemic mixtures of N-(acetyl)-4-keto-D,L-proline methyl esters (Example 7) or N-(methoxycarbonyl)-4,4-dimethoxy-D,L-proline methyl esters (Example 8) could not be resolved with high enantioselectivity using either CALB, or any of the other commercially-available esterases, lipases, and proteases which were screened.

Isolating the N-(alkoxycarbonyl)-4-keto-D-proline alkyl ester from the reaction product, N-(alkoxycarbonyl)-4-keto-D-proline, is readily performed (e.g., by extraction), and reducing the keto-group of the isolate with an appropriate reducing agent yields the corresponding N-(alkoxycarbonyl)-cis-4-hydroxy-D-proline alkyl ester, a compound readily hydrolyzed to produce CHDP in high yield and purity.

B. Enzymatic resolution of 4-hydroxyproline derivatives.

Depending on the starting materials chosen, the chemical synthesis of 4-hydroxyproline derivatives from inexpensive starting materials can produce a mixture of two or more of four possible diastereomers. Diastereomeric mixtures of N-(methoxycarbonyl)-4-hydroxyproline methyl esters have been screened against a variety different commercial protease, lipase and esterase enzyme preparations, and only CALB was found to hydrolyze the methyl ester of the L-isomer of several different diastereomeric mixtures with high ($\geq 95\%$ diastereomeric excess (de) of remaining substrate) diastereomeric selectivity at 50% conversion. The four diastereomers of N-(methoxycarbonyl)-4-hydroxyproline methyl ester are N-(methoxycarbonyl)-cis-4-hydroxy-D-proline methyl ester (CHDP(MEMC)), N-(methoxycarbonyl)-cis-4-hydroxy-L-proline methyl ester (CHLP(MEMC)), N-(methoxycarbonyl)-trans-4-hydroxy-D-proline methyl ester (THDP(MEMC)), and N-(methoxycarbonyl)-trans-4-hydroxy-L-proline methyl ester (THLP(MEMC)):

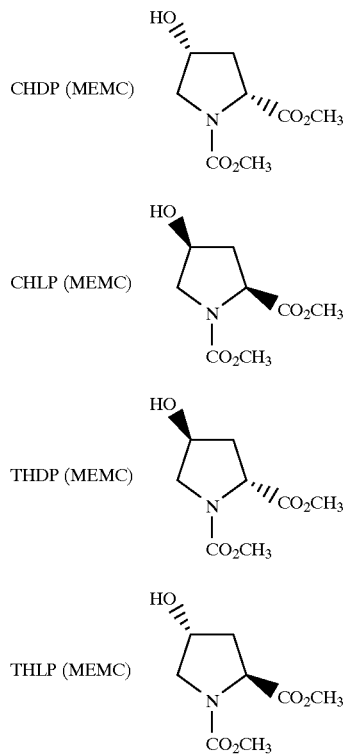

Using CALB for the diastereomeric resolution of five of the six possible pairs of diastereomers of N-(methoxycarbonyl)-4-hydroxyproline methyl esters produced the diastereomeric excesses at the indicated conversions listed in Table 1 below.

TABLE 1

Diastereomeric excess (de) of remaining substrate and conversion for the CALB-catalyzed resolution of diastereomeric mixtures of N-(methoxycarbonyl)-4-hydroxyproline methyl esters.

| 1:1 mixture of diastereomers | conversion (%) | % de substrate |
|---|---|---|
| CHDP(MEMC)/THLP(MEMC) | 50 | 100% CHDP(MEMC) |
| CHDP(MEMC)/CHLP(MEMC) | 52 | 100% CHDP(MEMC) |
| THDP(MEMC)/THLP(MEMC) | 52 | 100% THDP(MEMC) |
| CHLP(MEMC)/THLP(MEMC) | 57 | 100% CHLP(MEMC) |
| CHLP(MEMC)/THDP(MEMC) | 57 | 93% THDP(MEMC) |

Of the six possible pairs of diastereomers of N-(methoxycarbonyl)-4-hydroxyproline methyl esters, three could be separated with 100% de at 50–52% conversion, and an additional two pairs could be separated with a de of 100% or 93% at slightly greater than 50% conversion. This unanticipated result was due to the large differences in the relative rates of methyl ester hydrolysis of each of the four diastereomers according to the following order: THLP(MEMC)>CHLP(MEMC)>THDP(MEMC)>CHDP(MEMC), where no hydrolysis of CHDP(MEMC) by CALB under reaction conditions was observed. Because of the relatively slow rate of hydrolysis of THDP(MEMC) by CALB relative to THLP(MEMC) and CHLP(MEMC), no attempt was made to resolve a 1:1 mixture of CHDP(MEMC) and THDP(MEMC), although such a resolution with high diastereomeric excess for THDP(MEMC) is possible if the concentration of CALB employed were high enough.

Two alternate 4-hydroxyproline derivatives, N-(ethoxycarbonyl)-trans-4-hydroxy-L-proline methyl ester (THLP(MEEC)) and N-(tert-butoxycarbonyl)-trans-4-hydroxy-L-proline methyl ester (THLP(MEBOC)), were also prepared, and CALB was found to also hydrolyze the methyl esters of these derivatives. A comparison of the rate of hydrolysis of THLP(MEMC), THLP(MEEC), and THLP(MEBOC) by CALB was performed; the initial rate of methyl ester hydrolysis of THLP(MEEC) was approximately 3.3 times faster than THLP(MEEC), which in turn was ca 1.7 times faster than THLP(MEBOC).

DESCRIPTION OF THE PREFERRED EMBODIMENTS

Methods and Materials

The *Candida antartica* lipase B (CALB) can isolated from *Candida antartica* cells following published procedures (Patkar et al., *Ind J. Chem., Sect. B* 32B:76–80 (1993)) or obtained from commercial sources (e.g., SP 525 from NOVO Nordisk; CHIRAZYME® L-2 from Boehringer Mannheim) and used as catalyst without any pretreatment. CALB can also be immobilized in a polymer matrix, on a soluble or insoluble organic support (e.g. NOVOZYM® 435 from Novo Nordisk), or on an insoluble inorganic support which simplifies catalyst recovery for reuse; these immobilization methods have been widely reported and are well-known to those skilled-in-the-art. Membrane separation of the soluble enzyme from the reaction mixture may also be employed. Lipases with a substrate activity and enantiospecificity similar to that of CALB can also be employed in the present invention, as well as genetically-engineered whole-cell transformants which express CALB.

The amount of unimmobilized or immobilized CALB (mg/mL) in the reaction mixture is chosen to obtain the desired rate of reaction. The weight of unimmobilized CALB (as crude enzyme preparation, not purified protein) in the hydrolysis reactions of the present invention typically ranges from 0.1 mg to 50 mg of CALB per mL of total reaction volume, preferably from 1 mg to 20 mg of CALB per mL of total reaction volume. The amount of immobilized CALB (mg/mL) in the reaction mixture is also chosen to obtain the desired rate of reaction, and is dependent on the specific activity of the immobilized enzyme catalyst. The weight of immobilized CALB (as crude enzyme preparation, not purified protein) in the hydrolysis reactions of the present invention typically ranges from 0.1 mg to 1.0 g of immobilized CALB per mL of aqueous reaction mixture, preferably from 1 mg to 200 mg of CALB per mL of aqueous reaction mixture. In the case of immobilized CALB the reaction can also be run by passing the aqueous solution containing the keto- or hydroxy-proline derivatives through a column containing the immobilized enzyme.

Concentrations of mixtures of the ketoproline or hydroxyproline derivatives in reactions described by the present invention may vary, and include concentrations up to and including their solubility limit in the reaction mixture. The solubility of the ketoproline or hydroxyproline derivatives is dependent on several parameters, including the temperature of the solution and the salt concentration (buffer and/or hydrolysis products) in the aqueous phase. A preferred range of initial concentration of ketoproline or hydroxyproline mixtures is from 50 mM to 500 mM, but higher concentrations may also be employed. The hydrolysis reactions may also be performed using a reaction mixture which is initially composed of two phases: an aqueous phase containing the enzyme catalyst and dissolved ketoproline or hydroxyproline derivatives (and optionally a buffer), and an organic phase (containing additional undissolved ketoproline or hydroxyproline derivatives); as the reaction progresses, the starting material dissolves into the aqueous phase, and eventually complete conversion of one isomer is obtained. The reaction can also be run in a reaction mixture which consists primarily of an organic solvent to which is added at least the minimal amount of water required for both the hydrolysis reaction and for maintaining enzyme activity. In addition, the reaction can also be run using a single phase aqueous mixture comprising water and a polar organic solvent miscible with water. The hydrolysis reactions may be carried out in a single batch reaction, or in a continuous process.

The temperature of the hydrolysis reaction is chosen to optimize the reaction rate, the stability of the enzyme catalyst activity, and the stability of the ketoproline or hydroxyproline derivatives. The temperature of the reaction may range from just above the freezing point of the suspension (approximately 0° C.) to 60° C., with a preferred range of reaction temperature of from 15° C. to 45° C.

The pH of the reaction mixture is also chosen to optimize the reaction rate, the stability of the enzyme catalyst activity, and the stability of the ketoproline or hydroxyproline derivatives. The stability of aqueous solutions of N-(alkoxycarbonyl)-4-ketoproline alkyl esters or N-(alkoxycarbonyl)-4-hydroxyproline alkyl esters were dependent on pH. Solutions of N-(alkoxycarbonyl)-4-ketoproline alkyl esters were most stable within the pH range of from pH 2.0 to pH 6.0, with a loss of starting material in the absence of enzyme observed at a pH greater that 6.0. Solutions of N-(alkoxycarbonyl)-4-hydroxyproline alkyl esters were most stable within the pH range of from pH 2.0 to pH 7.5, with a loss of starting material in the absence of enzyme observed at a pH greater than 7.5. The ester hydrolysis products of these mixtures were more stable at any given pH than the corresponding ester. CALB showed no enzymatic activity at pH 2.0, and increasing activity with increasing pH between pH 3.0 and 8.0; no loss of CALB activity was observed between pH 4.0 and 8.0 after 21 h. For resolution of mixtures of N-(alkoxycarbonyl)-4-keto-D,L-proline alkyl esters, a pH range of from 3.0 to 6.0 is preferred, and a pH range of from 4.0 to 5.0 is most preferred. For resolution of diastereomeric mixtures of N-(alkoxycarbonyl)-4-hydroxyproline alkyl esters, a pH range of from 3.0 to 7.5 is preferred, and a pH range of from 6.0 to 7.0 is most preferred.

Maintaining the initial pH of the reaction mixture is done by adding an appropriate buffer having a pKa within approximately one pH unit of the reaction mixture and at a sufficient concentration. For a reaction pH of 5.0, 6.0, and 7.0, an acetate, succinate and phosphate buffer, respectively, have been employed; the choice of buffer is not limited to these examples. The reaction may also be run in the absence of added buffer, where the pH of the reaction mixture is monitored over the course of the reaction and acid or base added to maintain the pH of the reaction mixture at the desired value.

Separating the components from the CALB-catalyzed enzymatic resolution of a mixture of two N-(alkoxycarbonyl)-4-ketoproline alkyl esters or two N-(alkoxycarbonyl)hydroxyproline alkyl esters may readily be accomplished by exploiting the difference in chemical properties of an alkyl ester relative to a carboxylic acid or carboxylic acid salt. The unhydrolyzed alkyl ester can be readily extracted from the aqueous reaction mixture with any of a variety of organic solvents, including (but not limited to) dichloromethane, chloroform, toluene, methyl tert-butyl ether, or diisopropyl ether, while the N-(alkoxycarbonyl)-4-ketoproline or N-(alkoxycarbonyl)-hydroxyproline remains in the aqueous phase as the carboxylic acid (or carboxylic acid salt, depending on pH of the aqueous reaction mixture). Other methods of separation could include ion exchange chromatography, electrodialysis, selective precipitation, or fractional crystallization.

Reduction of the isolated N-(alkoxycarbonyl)-4-keto-D-proline alkyl ester to produce N-(alkoxycarbonyl)-cis-4-hydroxy-D-proline alkyl ester may be accomplished by a variety of methods, including but not limited to hydrogenation, reduction using metal hydride reducing agents, or enzymatic or microbial reduction. Catalytic hydrogenation is a preferred method for ultimately preparing CHDP from an N-(alkoxycarbonyl)-4-keto-D-proline alkyl ester. A solution of an N-(alkoxycarbonyl)-4-keto-D-proline alkyl ester (prepared by enzymatic resolution of a racemic mixture of N-(alkoxycarbonyl)-4-keto-D,L-proline alkyl esters) in an aqueous or organic solvent is prepared at an initial concentration of from 1 weight percent to at least 50 weight percent of the solution, with a preferred range of from 7.5 weight percent to 25 weight percent. To the solution described above is then added a suitable hydrogenation catalyst which will produce as the predominant product N-(alkoxycarbonyl)-cis-4-hydroxy-D-proline alkyl ester in an amount equal to from 0.1% to at least 20% by weight of the amount of the N-(alkoxycarbonyl)-4-keto-D-proline alkyl ester present. The resulting mixture is then contacted with hydrogen gas at a suitable temperature and pressure to convert the N-(alkoxycarbonyl)-4-keto-D-proline alkyl ester to the corresponding N-(alkoxycarbonyl)-cis-4-hydroxy-D-proline alkyl ester. Hydrogenation catalysts suitable for this purpose include (but are not limited to) platinum oxide, platinum on alumina, and Raney nickel.

Hydrolysis of the isolated N-(alkoxycarbonyl)-4-hydroxyproline alkyl ester to produce CHDP, CHLP, THDP or THLP may be accomplished by a variety of methods and are well-known to those skilled-in-the-art. Specifically, hydrolysis of the isolated N-(alkoxycarbonyl)-cis-4-hydroxy-D-proline alkyl ester to produce CHDP may be accomplished by, but is not limited to, refluxing in 6N HCl overnight.

In the following examples, which serve to further illustrate the invention, analysis of mixtures of cis- and trans-isomers of N-(alkoxycarbonyl)-4-hydroxy-D-proline alkyl esters (and cis and trans mixtures of the corresponding L-proline derivatives), and the hydrolysis products (mixtures of cis- and trans-isomers of N-(alkoxycarbonyl)-4-hydroxy-D(or L)-prolines) were performed by HPLC using a Bio-Rad HPX-87H column (30 cm×7.8 mm dia.) with refractive index detector or UV detector at 210 nm, using 0.005N sulfuric acid as solvent. Mixtures of N-(alkoxycarbonyl)-4-keto-D,L-proline alkyl esters were analyzed for percent conversion by gas chromatography on a DB-1701 capillary column (30 m×0.53 mm ID, 1 micron film thickness). Chiral gas chromatography for the separation mixtures of N-(alkoxycarbonyl)-4-keto-D,L-proline alkyl esters, N-(alkoxycarbonyl)-cis-4-hydroxy-D,L-proline alkyl esters, and N-(alkoxycarbonyl)-trans-4-hydroxy-D,L-proline alkyl esters was performed using either an Astec G TA Trifluoroacetyl gamma-cyclodextrin capillary column (30 m or 50 m×0.25 mm). The commercial enzymes listed in the Examples below were obtained from Sigma or Boehringer Mannheim.

Weights reported in the following Examples for soluble CALB and all other enzyme preparations are for the crude enzyme preparations; for example, the CALB protein was approximately 15 wt % of the total crude enzyme preparation of CHIRAZYME® L-2 from Boehringer Mannheim. The meaning of abbreviations is as follows: "sec" means second(s), "min" means minute(s), "h" means hour(s), "d" means day(s), "$\mu$l" means microliter, "mL" means milliliters, "L" means liters, "mM" means millimolar, "M" means molar, "mmol" means millimole(s).

EXAMPLE 1

Enzyme Screens for Resolution of Racemic N-(methoxycarbonyl)-4-Keto-D,L-Proline Methyl Ester An aqueous solution (1.0 mL) containing 0.100M racemic N-(methoxycarbonyl)-4-keto-D,L-proline methyl ester in either 0.20M sodium succinate (pH 6.0) or 0.20M sodium acetate (pH 5.0) was mixed with 5.0 to 50 mg/mL of commercial enzyme preparations (listed in the table below) at 25° C. The reactions were analyzed after 5 h (pH 6.0) or 24 h (pH 5.0) by removal of 0.200 mL samples followed by rapid mixing of the samples with an equivalent volume of 20 mM hexadecane (GC internal standard) in dichloromethane for 3 minutes, which resulted in the complete extraction of the unreacted D- and L-enantiomers of the N-(methoxycarbonyl)-4-ketoproline methyl esters. The dichloromethane extract was then analyzed by chiral gas chromatography on a Chiraldex G-TA column (Advanced Separation Technologies, Inc., 50 m×0.32 mm ID) to determine the percent conversion of the racemate, and the enantiomeric excess of the N-(methoxycarbonyl)-4-keto-D-proline methyl ester. Optimum conversion and enantiomeric excess of the D-isomer (obtained with all proteases or lipases), or the L-isomer (obtained with porcine liver esterase) are listed in Table 2 below.

TABLE 2

| enzyme | source | conv. | % ee |
|---|---|---|---|
| protease, type I | bovine pancreas | 0 | 0 |
| protease, type II | Aspergillus oryzae | 0 | 0 |
| protease, type IV | Streptomyces caespitosus | 0 | 0 |
| protease, type VIII | Bacillus licheniformis | 32 | 23 |
| protease, type IX | Bacillus polymyaxa | 0 | 0 |
| protease, type X | B. thermoproteoliticus rokko | 0 | 0 |
| protease, type XIII | Aspergillus saitoi | 0 | 0 |
| protease, type XIV | Streptomyces griseus | 0 | 0 |
| protease | Bacillus licheniformis | 30 | 20 |
| protease, type XVIII | Rhizopus sp. (Newlase) | 0 | 0 |
| protease, type XIX | Aspergillus sojae | 0 | 0 |
| protease, type XXI | Streptomyces griseus | 0 | 0 |
| protease, type XXIII | Aspergillus oryzae | 17 | 13 |
| protease, type XXIV | bacterial (subtil. Carlsberg) | 17 | 18 |
| protease, type XXVII | (Nagarase) | 27 | 21 |
| protease, type XXXI | Bacillus licheniformis | 15 | 0 |
| protease (Chirazyme P1) | Bacillus licheniformis | 54 | 65 |
| protease, bromelain | pineapple stem | 0 | 0 |
| protease, chymopapain | papaya latex | 0 | 0 |
| protease, α-chymotrypsin | bovine pancreas, Type I-S | 0 | 0 |
| protease, α-chymotrypsin | bovine pancreas, Type II | 0 | 0 |
| protease, β-chymotrypsin | bovine pancreas | 0 | 0 |
| protease, γ-chymotrypsin | bovine pancreas | 0 | 0 |
| protease, δ-chymotrypsin | bovine pancreas | 0 | 0 |
| protease, papain | papaya latex | 0 | 0 |
| protease, pepsin | porcine stomach mucosa | 0 | 0 |
| protease, trypsin | bovine pancreas | 0 | 0 |
| protease, trypsin | porcine pancreas | 0 | 0 |
| lipase, type I | wheat germ | 0 | 0 |
| lipase, type II | porcine pancreas | 0 | 0 |
| lipase, type XI | Rhizopus arrhizus | 0 | 0 |
| lipase, type XII | Chromobacterium viscosum | 0 | 0 |
| lipase, type XIII | Pseudomonas sp. | 0 | 0 |
| lipase (Chirazyme L1) | Burkholderia sp. | 0 | 0 |
| lipase (Chirazyme L2) | Candida antartica, fraction B | 51 | 95 |
| lipase (Chirazyme L3) | Candida rugosa | 0 | 0 |
| lipase (Chirazyme L4) | Pseudomonas sp. | 0 | 0 |
| lipase (Chirazyme L5) | Candida antartica, fraction A | 16 | 12 |
| lipase (Chirazyme L6) | Pseudomonas sp. | 0 | 0 |
| lipase (Chirazyme L7) | porcine pancreas | 0 | 0 |
| lipase (Chirazyme L8) | Humicola sp. | 0 | 0 |
| esterase | porcine liver | 63 | 33 |
| esterase (Chirazyme E1) | porcine liver, fraction 1 | 70 | 12 |
| esterase (Chirazyme E2) | porcine liver, fraction 2 | 31 | 5 |

EXAMPLE 2

Enzymatic Resolution of Racemic N-(Methoxycarbonyl)-4-Keto-D,L-Proline Methyl Ester The procedure described in Example I was repeated using Candida antartica lipase fraction B (CALB), except that the reaction was run in 0.200M sodium cetate (pH 5.0) instead of the 0.20M sodium succinate buffer (pH 6.0) used for Candida antartica lipase fraction B in Example 1. Aqueous solutions ( 5.0 mL) containing varying concentrations of a racemic mixture of N-(methoxycarbonyl)-4-keto-D,L-proline methyl ester and CALB were mixed at 15° C., 25° C., 35° C. or 45° C. Optimum conversion of the racemate, and enantiomeric excess of the D-isomer are listed in Table 3 below.

TABLE 3

| racemate conc. (mM) | enzyme (mg/mL) | temp. (° C.) | time (h) | racemate conv. (%) | ee D-isomer (%) |
|---|---|---|---|---|---|
| 100 | 20 | 15 | 24 | 51 | 100 |
| 100 | 10 | 25 | 24 | 51 | 100 |
| 200 | 6.7 | 35 | 29 | 51 | 97 |

TABLE 3-continued

| racemate conc. (mM) | enzyme (mg/mL) | temp. (° C.) | time (h) | racemate conv. (%) | ee D-isomer (%) |
|---|---|---|---|---|---|
| 100 | 20 | 45 | 6 | 50 | 100 |
| 300 | 31 | 45 | 23 | 48 | 99 |

EXAMPLE 3

Enzymatic Resolution of Racemic N-(Methoxycarbonyl)-4-Keto-D,L-Proline Methyl Ester with Immobilized Enzyme An aqueous solution (5.0 mL) containing 25 mM N-(methoxycarbonyl)-4-keto-Dproline methyl ester and 25 mM N-(methoxycarbonyl)-4-keto-L-proline methyl ester in 0.200M sodium acetate (pH 5.0) was mixed with 2.5 g of immobilized *Candida antartica* lipase fraction B (Boehringer Mannheim, CHIRAZYME® L-2, c.-f., C2, lyo.) at 25° C. The reaction mixture was analyzed after 31 h by mixing the entire reaction mixture with 5.0 mL of 20 mM hexadecane in dichloromethane for 10 minutes, which resulted in the complete extraction of the unreacted D- and L-isomers. The dichloromethane extract was then analyzed by chiral gas chromatography on a Chiraldex G-TA column (Advanced Separation Technologies, Inc., 50 m×0.32 mm ID) to determine the amounts of the unreacted D- and L-isomers. After 31 h, an 85% enantiomeric excess of N-(methoxycarbonyl)-4-keto-D-proline methyl ester was obtained at 41% conversion of the racemic mixture.

EXAMPLE 4

Isolation of N-(Methoxycarbonyl)-4-Keto-D-Proline Methyl Ester by Enzymatic Resolution of Racemic N-(Methoxycarbonyl)-4-Keto-D,L-Proline Methyl Ester A 200 mL aqueous solution containing 0.200M sodium acetate (pH 5.0), 1.3325 g of *Candida antartica* lipase fraction B, and 4.02 g of racemic N-(methoxycarbonyl)-4-keto-D,L-proline methyl ester (100 mM) was stirred at 25° C. After 24 h, an 96% enantiomeric excess of N-(methoxycarbonyl)-4-keto-D-proline methyl ester was obtained at 50% conversion of the racemic mixture. The reaction mixture was filtered using a 10,000 MWCO membrane filter (Amicon) to remove the enzyme catalyst, and the filtrate extracted with three 200 mL portions of dichloromethane. The combined organic extracts were dried over magnesium sulfate, filtered, and the dichloromethane removed from the filtrate by rotary evaporation at reduced pressure. Residual dichloromethane was removed from the resulting colorless oil at high vacuum (50 millitorr) to produce N-(methoxycarbonyl)-4-keto-D-proline methyl ester as a white solid (1.99 g, 99% isolated yield, 99% purity (by GC), 97% ee).

EXAMPLE 5

Enzymatic Resolution of a Racemic Mixture of N-(Ethoxycarbonyl)-4-Keto-D.L-Proline Ethyl Ester An aqueous solution (2.0 mL) containing 50 mM N-(ethoxycarbonyl)-4-keto-D-proline ethyl ester and 50 mM N-(ethoxycarbonyl)-4-keto-L-proline ethyl ester in 0.200M sodium acetate (pH 5.0) and 30 mg/mL of *Candida antartica* lipase fraction B was mixed at 25° C. The reaction mixture was analyzed by mixing 0.200 mL aliquots of the reaction mixture with an equivalent volume of 20 mM hexadecane in dichloromethane for 3 minutes, which resulted in the complete extraction of the unreacted D- and L-isomers. The dichloromethane extract was then analyzed by chiral gas chromatography on a Chiraldex G-TA column (Advanced Separation Technologies, Inc., 50 m×0.32 mm ID) to determine the amounts of the unreacted D- and L-isomers. After 24 h, a 100% enantiomeric excess of N-(ethoxycarbonyl)-4-keto-D-proline ethyl ester was obtained at 51% conversion of the racemic mixture.

EXAMPLE 6

Enzymatic Resolution of a Racemic Mixture of N-(2-Phenylacetyl)-4-Keto-D,L-Proline Methyl Ester An aqueous solution (1.0 mL) containing 19 mM of N-(2-phenylacetyl)-4-keto-D-proline methyl ester and 19 mM of N-(2-phenylacetyl)-4-keto-L-proline methyl ester in 0.200M sodium acetate (pH 5.0) and 25 mg/mL of *Candida antartica* lipase fraction B was mixed at 25° C. The reaction mixture was analyzed by mixing with an equivalent volume of 20 mM hexadecane in dichloromethane for 3 minutes, which resulted in the complete extraction of the unreacted D- and L-isomers. The dichloromethane extract was then analyzed by chiral gas chromatography on a Chiraldex G-TA column (Advanced Separation Technologies, Inc., 50 m×0.32 mm ID) to determine the relative amounts of the unreacted D- and L-isomers. After 28 h, 97% of the D-isomer and 28% of the L-isomer remained, yielding a 55% enantiomeric excess of the D-isomer at 38% conversion of the racemic mixture (E=28).

EXAMPLE 7

Enzyme Screens for Resolution of Racemic N-(Acetyl)-4-Keto-D,L-Proline Methyl Ester (Comparative Example)

An aqueous solution (1.0 mL) containing 0.100M racemic N-(acetyl)-4-keto-D,L-proline methyl ester in 0.20M sodium succinate (pH 6.0) was mixed with 5.0 to 30 mg/mL of commercial enzyme preparations (listed in the table below) at 25° C. The reactions were analyzed after 5 h by removal of 0.200 mL samples followed by rapid mixing of the samples with an equivalent volume of 20 mM hexadecane (GC internal standard) in dichloromethane for 3 minutes, which resulted in the complete extraction of the unreacted D- and L-isomers of N-(acetyl)-4-ketoproline methyl esters. The dichloromethane extract was then analyzed by chiral gas chromatography on a Chiraldex G-TA column (Advanced Separation Technologies, Inc., 50 m×0.32 mm ID) to determine the percent conversion of the racemate, and the enantiomeric excess of the N-(acetyl)-4-keto-D-proline methyl ester. Optimum conversion and enantiomeric excess of the D-isomer are listed in Table 4 below.

TABLE 4

| enzyme | source | conv. | % ee |
|---|---|---|---|
| protease, type I | bovine pancreas | 0 | 0 |
| protease, type II | *Aspergillus oryzae* | 0 | 0 |
| protease, type IV | *Streptomyces caespitosus* | 0 | 0 |
| protease, type IX | *Bacillus polymyxa* | 0 | 0 |
| protease, type X | *B. thermoproteoliticus rokko* | 0 | 0 |
| protease, type XIII | *Aspergillus saitoi* | 0 | 0 |
| protease, type XIV | *Streptomyces griseus* | 13 | 3 |
| protease, type XV | *Bacillus licheniformis* | 13 | 8 |

TABLE 4-continued

| enzyme | source | conv. | % ee |
|---|---|---|---|
| protease, type XIX | Aspergillus sojae | 0 | 0 |
| protease, type XXI | Streptomyces griseus | 12 | 6 |
| protease, type XXIII | Aspergillus oryzae | 23 | 20 |
| protease, type XXXI | Bacillus licheniformis | 14 | 5 |
| protease (Chirazyme P1) | Bacillus licheniformis | 43 | 37 |
| protease, bromelain | pineapple stem | 0 | 0 |
| protease, chymopapain | papaya latex | 0 | 0 |
| protease, papain | papaya latex | 0 | 0 |
| protease, pepsin | porcine stomach mucosa | 0 | 0 |
| protease, trypsin | bovine pancreas | 0 | 0 |
| protease, trypsin | porcine pancreas | 0 | 0 |
| protease, α-chymotrypsin | bovine pancreas, Type I-S | 0 | 0 |
| protease, α-chymotrypsin | bovine pancreas, Type II | 0 | 0 |
| protease, β-chymotrypsin | bovine pancreas | 0 | 0 |
| protease, γ-chymotrypsin | bovine pancreas | 0 | 0 |
| protease, δ-chymotrypsin | bovine pancreas | 0 | 0 |
| lipase | Candida cylindracea | 0 | 0 |
| lipase (Chirazyme L1) | Burkholderia sp. | 0 | 0 |
| lipase (Chirazyme L2) | Candida antartica, fraction B | 0 | 0 |
| lipase (Chirazyme L3) | Candida rugosa | 0 | 0 |
| lipase (Chirazyme L4) | Pseudomonas sp. | 0 | 0 |
| lipase (Chirazyme L5) | Candida antartica, fraction A | 0 | 0 |
| lipase (Chirazyme L6) | Pseudomonas sp. | 0 | 0 |
| lipase (Chirazyme L7) | porcine pancreas | 0 | 0 |
| lipase (Chirazyme L8) | Humicola sp. | 0 | 0 |
| esterase | porcine liver | 0 | 0 |

EXAMPLE 8

Enzyme Screens for Resolution of Racemic N-(Methoxycarbonyl)-4,4-Dimethoxy-D,L-Proline Methyl Ester (Comparative Example)

An aqueous solution (1.0 mL) containing 0.100M racemic N-(methoxycarbonyl)-4,4-dimethoxy-D,L-proline methyl ester in 0.25M potassium phosphate (pH 7.0) was mixed with 5.0 to 30 mg/mL of commercial enzyme preparations (listed in the table below) at 25° C. The reactions were analyzed after 6 h or 17 h by removal of 0.200 mL samples followed by rapid mixing of the samples with an equivalent volume of 50 mM hexadecane (GC internal standard) in ethyl acetate for 3 minutes, which resulted in the extraction of the N-(methoxycarbonyl)-4,4-dimethoxy-D,L-proline methyl esters. The ethyl acetate extract was then analyzed by chiral gas chromatography on a Chiraldex G-TA column (Advanced Separation Technologies, Inc., 50 m×0.32 mm ID) to determine the percent conversion of the racemate, and the enantiomeric excess of N-(methoxycarbonyl)-4,4-dimethoxy-D-proline methyl ester. Optimum conversion and enantiomeric excess of the D-isomer for each enzyme are listed in Table 5 below.

TABLE 5

| enzyme | source | conv. | % ee |
|---|---|---|---|
| protease, type XXIV | bacterial (subtil. Carlsberg) | 42 | 22 |
| protease, type XXVII | (Nagarase) | 44 | 30 |
| protease (Chirazyme P1) | Bacillus licheniformis | 44 | 22 |
| protease, trypsin | bovine pancreas | 0 | 0 |
| lipase (Chirazyme L1) | Burkholderia sp. | 0 | 0 |
| lipase (Chirazyme L2) | Candida antartica, fraction B | 0 | 0 |
| lipase (Chirazyme L3) | Candida rugosa | 0 | 0 |
| lipase (Chirazyme L4) | Pseudomonas sp. | 0 | 0 |
| lipase (Chirazyme L5) | Candida antartica, fraction A | 0 | 0 |
| lipase (Chirazyme L6) | Pseudomonas sp. | 0 | 0 |
| lipase (Chirazyme L7) | porcine pancreas | 10 | 0 |
| lipase (Chirazyme L8) | Humicola sp. | 0 | 0 |
| esterase | Arthrobacter sp. | 20 | 3 |

TABLE 5-continued

| enzyme | source | conv. | % ee |
|---|---|---|---|
| esterase | porcine liver | 48 | 63 |
| esterase (Chirazyme E1) | porcine liver, fraction 1 | 59 | 85 |
| esterase (Chirazyme E2) | porcine liver, fraction 2 | 64 | 91 |

EXAMPLE 9

Enzyme Screens for Resolution of Diastereomeric Mixtures of N-(Methoxycarbonyl)-Cis-4-Hydroxy-D-Proline Methyl Ester and N-(Methoxycarbonyl)-Trans-4-Hydroxy-L-Proline Methyl Ester An aqueous solution (1.0 mL) containing 0.050M N-(methoxycarbonyl)-trans-4-hydroxy-L-proline methyl ester and 0.050M N-(methoxycarbonyl)-cis-4-hydroxy-D-proline methyl ester in 0.100M potassium phosphate (pH 7.0) was mixed with 5.0 to 50 mg/mL of commercial enzyme preparations (listed in the table below) at 25° C. The reactions were analyzed after 5 h or 24 h by removal of a 0.200 mL sample and mixing with an equivalent volume of 0.100M propionic acid (HPLC internal standard) in water. The resulting solution was filtered through a 10K molecular weight cut-off filter to remove the enzyme and the filtrate analyzed by high pressure liquid chromatography on a HPX-87H column (Bio-Rad, 30 cm×7.8 mm) to determine the percent conversion of each isomer of the diastereomeric mixture, and the diastereomeric excess of the N-(methoxycarbonyl)-cis-4-hydroxy-D-proline methyl ester. Optimum conversion and diastereomeric excess of the D-isomer are listed in Table 6 below.

TABLE 6

| enzyme | source | conv. | % de |
|---|---|---|---|
| protease, type I | bovine pancreas | 0 | 0 |
| protease, type II | Aspergillus oryzae | 0 | 0 |
| protease, type IV | Streptomyces caespitosus | 0 | 0 |
| protease, type VIII | Bacillus licheniformis | 16 | 16 |
| protease, type IX | Bacillus polymyaxa | 0 | 0 |
| protease, type X | B. thermoproteoliticus rokko | 0 | 0 |
| protease, type XIII | Aspergillus saitoi | 0 | 0 |
| protease, type XIV | Streptomyces griseus | 0 | 0 |
| protease | Bacillus licheniformis | 0 | 0 |
| protease, type XVIII | Rhizopus sp. Newlase) | 0 | 0 |
| protease, type XIX | Aspergillus sojae | 0 | 0 |
| protease, type XXI | Streptomyces griseus | 0 | 0 |
| protease, type XXIII | Aspergillus oryzae | 3 | 2 |
| protease, type XXIV | bacterial (subtil. Carlsberg) | 16 | 16 |
| protease, type XXVII | (Nagarase) | 2 | 4 |
| protease, type XXXI | Bacillus licheniformis | 0 | 0 |
| protease (Chirazyme P1) | Bacillus licheniformis | 28 | 26 |
| protease, bromelain | pineapple stem | 0 | 0 |
| protease, chymopapain | papaya latex | 0 | 0 |
| protease, α-chymotrypsin | bovine pancreas, Type I-S | 0 | 0 |
| protease, α-chymotrypsin | bovine pancreas, Type II | 0 | 0 |
| protease, β-chymotrypsin | bovine pancreas | 0 | 0 |
| protease, γ-chymotrypsin | bovine pancreas | 0 | 0 |
| protease, δ-chymotrypsin | bovine pancreas | 0 | 0 |
| protease, papain | papaya latex | 0 | 0 |
| protease, pepsin | porcine stomach mucosa | 0 | 0 |
| protease, trypsin | bovine pancreas | 0 | 0 |
| protease, trypsin | porcine pancreas | 0 | 0 |
| lipase, type I | wheat germ | 0 | 0 |
| lipase, type II | porcine pancreas | 0 | 0 |
| lipase, type XI | Rhizopus arrhizus | 0 | 0 |
| lipase, type XII | Chromobacterium viscosum | 0 | 0 |
| lipase, type XIII | Pseudomonas sp. | 0 | 0 |
| lipase (Chirazyme L1) | Burkholderia sp. | 0 | 0 |
| lipase (Chirazyme L2) | Candida antartica, fraction B | 50 | 100 |

TABLE 6-continued

| enzyme | source | conv. | % de |
|---|---|---|---|
| lipase (Chirazyme L3) | Candida rugosa | 0 | 0 |
| lipase (Chirazyme L4) | Pseudomonas sp. | 0 | 0 |
| lipase (Chirazyme L5) | Candida antartica, fraction A | 0 | 0 |
| lipase (Chirazyme L6) | Pseudomonas sp. | 0 | 0 |
| lipase (Chirazyme L7) | porcine pancreas | 0 | 0 |
| lipase (Chirazyme L8) | Humicola sp. | 0 | 0 |
| esterase | porcine liver | 28 | 12 |
| esterase (Chirazyme E1) | porcine liver, fraction 1 | 68 | 17 |
| esterase (Chirazyme E2) | porcine liver, fraction 2 | 29 | 11 |

EXAMPLE 10

Enzymatic Resolution of a Diastereomeric Mixture of N-(Methoxycarbonyl)-cis-4-Hydroxy-D-Proline Methyl Ester and N-(Methoxycarbonyl)-Trans-4-Hydroxy-L-Proline Methyl Ester A 3.0 mL aqueous solution containing 50 mM N-(methoxycarbonyl)-trans-4-hydroxy-L-proline methyl ester and 50 mM N-(methoxycarbonyl)-cis-4-hydroxy-D-proline methyl ester in 0.100M potassium phosphate (pH 7.0) was mixed with 2.1 mg/mL of *Candida antartica* lipase fraction B at 25° C. The reaction was analyzed by removal of a 0.200 mL sample and mixing with an equivalent volume of 0.100M propionic acid (HPLC internal standard) in water. The resulting solution was filtered through a 10K molecular weight cut-off filter to remove the enzyme and the filtrate analyzed by high pressure liquid chromatography on a HPX-87H column (Bio-Rad, 30 cm×7.8 mm) to determine the percent conversion of each isomer of the diastereomeric mixture, and the diastereomeric excess of the N-(methoxycarbonyl)-cis-4-hydroxy-D-proline methyl ester. After 24 h, a 100% diastereomeric excess of N-(methoxycarbonyl)-cis-4-hydroxy-D-proline methyl ester was obtained at 50% conversion of the diastereomeric mixture (no N-(methoxycarbonyl)-trans-4-hydroxy-L-proline methyl ester remained).

EXAMPLE 11

Enzymatic Resolution of a Diastereomeric Mixture of N-(Methoxycarbonyl)-Cis-4-Hydroxy-D-Proline Methyl Ester and N-(Methoxycarbonyl)-Trans-4-Hydroxy-L-Proline Methyl Ester with Immobilized Enzyme A 2.0 mL aqueous solution containing 50 mM N-(methoxycarbonyl)-trans-4-hydroxy-L-proline methyl ester and 50 mM N-(methoxycarbonyl)-cis-4-hydroxy-D-proline methyl ester in 0.100M potassium phosphate (pH 7.0) was mixed with 403 mg of immobilized *Candida antartica* lipase fraction B (Boehringer Mannheim, CHIRAZYME® L-2, c.-f., C2, lyo.) at 31° C. The reaction was analyzed by mixing the entire reaction mixture with an equivalent volume of 0.100M propionic acid (HPLC internal standard) in water for minutes. An aliquot of the resulting solution was filtered through a 10K molecular weight cut-off filter to remove the enzyme and the filtrate analyzed by high pressure liquid chromatography on a HPX-87H column (Bio-Rad, 30 cm×7.8 mm) to determine the percent conversion of each isomer of the distereomeric mixture, and the diastereomeric excess of the N-(methoxycarbonyl)-cis-4-hydroxy-D-proline methyl ester. After 7 h, a 94% diastereomeric excess of N-(methoxycarbonyl)-cis-4-hydroxy-D-proline methyl ester was obtained at 49% conversion of the diastereomeric mixture (3.2% N-(methoxycarbonyl)-trans-4-hydroxy-L-proline methyl ester remained).

EXAMPLE 12

Enzymatic Resolution of a Diastereomeric Mixture of N-(Methoxycarbonyl)-Cis-4-Hydroxy-L-Proline Methyl Ester and N-(Methoxycarbonyl)-Trans-4-Hydroxy-D-Proline Methyl Ester A 5.0 mL aqueous solution containing 51 mM N-(methoxycarbonyl)-trans-4-hydroxy-L-proline methyl ester and 51 mM N-(methoxycarbonyl)-cis-4-hydroxy-D-proline methyl ester in 0.100M potassium phosphate (pH 7.0) was mixed with 50 mg/mL of *Candida antartica* lipase fraction B at 25° C. The reaction was analyzed by removal of a 0.200 mL sample and mixing with an equivalent volume of 0.100M propionic acid (HPLC internal standard) in water. The resulting solution was filtered through a 10K molecular weight cut-off filter to remove the enzyme and the filtrate analyzed by high pressure liquid chromatography on a HPX-87H column (Bio-Rad, 30 cm×7.8 mm) to determine the percent conversion of each isomer of the diastereomeric mixture, and the diastereomeric excess of the N-(methoxycarbonyl)-trans-4-hydroxy-D-proline methyl ester. After 24 h, a 93% diastereomeric excess of N-(methoxycarbonyl)-trans-4-hydroxy-D-proline methyl ester was obtained at 57% conversion of the diastereomeric mixture (3.0% N-(methoxycarbonyl)-cis-4-hydroxy-L-proline methyl ester and 82.7% N-(methoxycarbonyl)-trans-4-hydroxy-D-proline methyl ester remained).

EXAMPLE 13

Enzyme Screens for Resolution of Diastereomeric Mixtures of N-(Methoxycarbonyl)-Cis-4-Hydroxy-L-Proline Methyl Ester and N-(Methoxycarbonyl)-Trans-4-Hydroxy-L-Proline Methyl Ester An aqueous solution containing 0.050M N-(methoxycarbonyl)-trans-4-hydroxy-L-proline methyl ester and 0.050M N-(methoxycarbonyl)-cis-4-hydroxy-L-proline methyl ester in 0.100M potassium phosphate (pH 7.0) was mixed with 5.0 to 50 mg/mL of commercial enzyme preparations (listed in the table below) at 25° C. The reactions were analyzed after 5 h by removal of a 0.200 mL sample and mixing with an equivalent volume of 0.100M propionic acid (HPLC internal standard) in water. The resulting solution was filtered through a 10K molecular weight cut-off filter to remove the enzyme and the filtrate analyzed by high pressure liquid chromatography on a HPX-87H column (Bio-Rad, 30 cm×7.8 mm) to determine the percent conversion of the diastereomeric mixture, and the diastereomeric excess of the N-(methoxycarbonyl)-cis-4-hydroxy-L-proline methyl ester. Optimum conversion and diastereomeric excess of the cis-L-isomer are listed in Table 7 below.

TABLE 7

| enzyme | source | conv. | % de |
|---|---|---|---|
| protease, type I | bovine pancreas | 0 | 0 |
| protease, type II | Aspergillus oryzae | 0 | 0 |
| protease, type IV | Streptomyces caespitosus | 0 | 0 |
| protease, type VIII | Bacillus licheniformis | 4 | 6 |
| protease, type IX | Bacillus polymyxa | 0 | 0 |
| protease, type X | B. thermoproteoliticus rokko | 0 | 0 |
| protease, type XIII | Aspergillus saitoi | 0 | 0 |

TABLE 7-continued

| enzyme | source | conv. | % de |
|---|---|---|---|
| protease, type XIV | Streptomyces griseus | 0 | 0 |
| protease | Bacillus licheniformis | 3 | 3 |
| protease, type XVIII | Rhizopus sp. (Newlase) | 0 | 0 |
| protease, type XIX | Aspergillus sojae | 0 | 0 |
| protease, type XXI | Streptomyces griseus | 0 | 0 |
| protease, type XXIII | Aspergillus oryzae | 0 | 0 |
| protease, type XXIV | bacterial (subtil. Carlsberg) | 6 | 5 |
| protease, type XXVII | (Nagarase) | 17 | 16 |
| protease, type XXXI | Bacillus licheniformis | 0 | 0 |
| protease (Chirazyme P1) | Bacillus licheniformis | 25 | 31 |
| protease, bromelain | pineapple stem | 0 | 0 |
| protease, chymopapain | papaya latex | 0 | 0 |
| protease, α-chymotrypsin | bovine pancreas, Type I-S | 0 | 0 |
| protease, α-chymotrypsin | bovine pancreas, Type II | 0 | 0 |
| protease, β-chymotrypsin | bovine pancreas | 0 | 0 |
| protease, γ-chymotrypsin | bovine pancreas | 0 | 0 |
| protease, δ-chymotrypsin | bovine pancreas | 0 | 0 |
| protease, papain | papaya latex | 6 | 2 |
| protease, pepsin | porcine stomach mucosa | 0 | 0 |
| protease, trypsin | bovine pancreas | 0 | 0 |
| protease, trypsin | porcine pancreas | 0 | 0 |
| lipase, type I | wheat germ | 0 | 0 |
| lipase, type II | porcine pancreas | 0 | 0 |
| lipase, type XI | Rhizopus arrhizus | 0 | 0 |
| lipase, type XII | Chromobacterium viscosum | 0 | 0 |
| lipase, type XIII | Pseudomonas sp. | 0 | 0 |
| lipase (Chirazyme L1) | Burkholderia sp. | 0 | 0 |
| lipase (Chirazyme L2) | Candida antartica, fraction B | 57 | 100 |
| lipase (Chirazyme L3) | Candida rugosa | 0 | 0 |
| lipase (Chirazyme L4) | Pseudomonas sp. | 0 | 0 |
| lipase (Chirazyme L5) | Candida antartica, fraction A | 0 | 0 |
| lipase (Chirazyme L6) | Pseudomonas sp. | 0 | 0 |
| lipase (Chirazyme L7) | porcine pancreas | 0 | 0 |
| lipase (Chirazyme L8) | Humicola sp. | 0 | 0 |
| esterase | porcine liver | 7 | 5 |
| esterase (Chirazyme E1) | porcine liver, fraction 1 | 58 | 94 |
| esterase (Chirazyme E2) | porcine liver, fraction 2 | 2 | 2 |

EXAMPLE 14

Relative Rates of Hydrolysis of N-(Alkoxycarbonyl)-Trans-4-Hydroxy-L-Proline Methyl Esters by CALB A 2.0 mL aqueous solution containing 50 mM N-(methoxycarbonyl)-trans-4-hydroxy-L-proline methyl ester, or 50 mM N-(ethoxycarbonyl)-trans-4-hydroxy-L-proline methyl ester, or 50 mM N-(tert-butoxycarbonyl)-trans-4-hydroxy-L-proline methyl ester in 0.100M potassium phosphate (pH 7.0) and 3.0 mg/mL of *Candida antartica* lipase fraction B was mixed at 25° C. The reactions were analyzed by removal of 0.200 mL aliquots at pre-determined times and mixing the sample with an equivalent volume of 0.100M propionic acid (HPLC internal standard) in water, and filtering the resulting solution through a 10K molecular weight cut-off filter to remove the enzyme. The filtrate was then analyzed by high pressure liquid chromatography on a HPX-87H column (Bio-Rad, 30 cm×7.8 mm) to determine the percent conversion of the N-(alkoxycarbonyl)-trans-4-hydroxy-L-proline methyl ester. Complete hydrolysis of the methyl ester of the N-methoxy-, N-ethoxy-, and N-tert-butoxycarbonyl derivatives occurred in 5 h, 2 h, and 6 h, respectively, and the initial reaction rates were 5.7, 18.7, and 3.3 micromoles/h/mg enzyme catalyst, respectively.

EXAMPLE 15

Enzymatic Resolution of a Diastereomeric Mixture of N-(Methoxycarbonyl)-Cis-4-Hydroxy-D,L-Proline Methyl Esters A 5.0 mL aqueous solution containing 50 mM N-(methoxycarbonyl)-cis-4-hydroxy-D-proline methyl ester and 50 mM N-(methoxycarbonyl)-cis-4-hydroxy-L-proline methyl ester in 0.100M potassium phosphate (pH 7.0) and 50 mg/mL of *Candida antartica* lipase fraction B was mixed at 25° C. The reaction was analyzed by removal of two 0.200 mL aliquots at pre-determined times. One 0.200 mL aliquot was mixed with an equivalent volume of 0.100M propionic acid (HPLC internal standard) in water, and the resulting solution filtered through a 10K molecular weight cut-off filter to remove the enzyme. The filtrate was then analyzed by high pressure liquid chromatography on a HPX-87H column (Bio-Rad, 30 cm×7.8 mm) to determine the total percent conversion of both the D- and L-proline isomers of the N-(methoxycarbonyl)-cis-4-hydroxyproline methyl esters. The second 0.200 mL aliquot was mixed with an equivalent volume of 20 mM hexadecane in dichloromethane for 3 minutes, which resulted in the partial extraction of the unreacted D- and L-proline isomers of the N-(methoxycarbonyl)-cis-4-hydroxyproline methyl esters. The dichloromethane extract was then analyzed by chiral gas chromatography on a Chiraldex G-TA column (Advanced Separation Technologies, Inc., 50 m×0.32 mm ID) to determine the relative amounts of the unreacted D- and L-isomers. After 47 h, a 100% enantiomeric excess of N-(methoxycarbonyl)-cis-4-hydroxy-D-proline methyl ester was obtained at 52% conversion of the diastereomeric mixture (no N-(methoxycarbonyl)-cis-4-hydroxy-L-proline methyl ester remained).

EXAMPLE 16

Enzymatic Resolution of a Diastereomeric Mixture of N-(Methoxycarbonyl)-Trans-4-Hydroxy-D,L-Proline Methyl Esters A 5.0 mL aqueous solution containing 50 mM N-(methoxycarbonyl)-trans-4-hydroxy-D-proline methyl ester and 50 mM N-(methoxycarbonyl)-trans-4-hydroxy-L-proline methyl ester in 0.100M potassium phosphate (pH 7.0) and 4.0 mg/mL of *Candida antartica* lipase fraction B was mixed at 25° C. The reaction was analyzed by removal of two 0.200 mL aliquots at pre-determined times. One 0.200 mL aliquot was mixed with an equivalent volume of 0.100M propionic acid (HPLC internal standard) in water, and the resulting solution filtered through a 10K molecular weight cut-off filter to remove the enzyme. The filtrate was then analyzed by high pressure liquid chromatography on a HPX-87H column (Bio-Rad, 30 cm×7.8 mm) to determine the total percent conversion of both the D- and L-isomers of N-(methoxycarbonyl)-trans-4-hydroxyproline methyl ester. The second 0.200 mL aliquot was mixed with an equivalent volume of 20 mM hexadecane in dichloromethane for 3 minutes, which resulted in the partial extraction of the unreacted D- and L-N-(methoxycarbonyl)-trans-4-hydroxyproline methyl esters. The dichloromethane extract was then analyzed by chiral gas chromatography on a Chiraldex G-TA column (Advanced Separation Technologies, Inc., 50 m×0.32 mm ID) to determine the relative amounts of the unreacted D- and L-isomers. After 24 h, a 100% diastereomeric excess of N-(methoxycarbonyl)-trans-4-hydroxy-D-proline methyl ester was obtained at 52% conversion of the diastereomeric mixture (no N-(methoxycarbonyl)-trans-4-hydroxy-L-proline methyl ester remained).

EXAMPLE 17

Hydrogenation of N-(Methoxycarbonyl)-4-Keto-D-Proline Methyl Ester to N-(Methoxycarbonyl)-Cis-4-Hydroxy-D-Proline Methyl Ester A 5.0 mL solution of 0.125 g of N-(methoxycarbonyl)-4-keto-D-proline methyl ester in ethyl acetate was mixed with 12.5 mg of 5% platinum on alumina under 70 psig of hydrogen at 25° C. After 18 h, the yields of N-(methoxycarbonyl)-cis-4-hydroxy-D-proline methyl ester and N-(methoxycarbonyl)-trans-4-hydroxy-D-proline methyl ester were 98.7% and 1.3%, respectively, with no N-(methoxycarbonyl)-4-keto-D-proline methyl ester remaining.

EXAMPLE 18

Hydrolysis of N-(Methoxycarbonyl)-Cis-4-Hydroxy-D-Proline Methyl Ester to Cis-4-Hydroxy-D-Proline (CHDP)

A solution of 0.125M N-(methoxycarbonyl)-cis-4-hydroxy-D-proline methyl ester in 6N HCl was refluxed for 16 h, then analyzed for CHDP and THLP using a Beckman Modal 6300 amino acid analyzer with post-column ninhydrin derivatization. The yields of CHDP and THLP were 98.0% and 2.0%, respectively, with no N-(methoxycarbonyl)-cis-4-hydroxy-D-proline methyl ester remaining.

What is claimed is:

1. A process for separating a racemic mixture of N-(alkoxycarbonyl)-4-keto-D,L-proline alkyl esters comprising (A) contacting in a reaction mixture a racemic mixture of formula I,

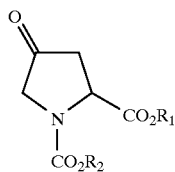

I where
      $R_1$ is selected from the group consisting of unsubstituted or substituted $C_1$–$C_6$ alkyl or alkenyl, and $C_3$–$C_6$ cycloalkyl, and
      $R_2$ is independently selected from the group consisting of unsubstituted or substituted $C_1$–$C_6$ alkyl or alkenyl, $C_3$–$C_6$ cycloalkyl, substituted or unsubstituted aryl alkyl, or substituted or unsubstituted heteroaryl alkyl,
    with an effective amount of the enzyme catalyst *Candida antarctica* lipase fraction B whereby the ester functionality of the corresponding L-isomer of the racemate is enantioselectively hydrolyzed.

2. The process of claim 1 wherein the reaction mixture is aqueous and has a pH of from about 3.0 to 6.0.

3. The process of claim 2 wherein the reaction mixture further comprises an organic phase comprising an immiscible organic solvent.

4. The process of claim 1 wherein the reaction mixture comprises a water-miscible organic solvent to which is added an effective amount of water for hydrolysis and enzyme activity.

5. A process for separating mixtures of diastereomeric pairs of N-(alkoxycarbonyl)-4-hydroxyproline alkyl esters comprising contacting in a reaction mixture a racemic mixture of formula II,

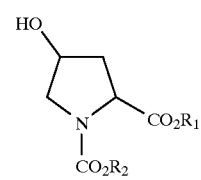

II where
      $R_1$ is selected from the group consisting of unsubstituted or substituted $C_1$–$C_6$ alkyl or alkenyl, and $C_3$–$C_6$ cycloalkyl, and
      $R_2$ is independently selected from the group consisting of unsubstituted or substituted $C_1$–$C_6$ alkyl or alkenyl, $C_3$–$C_6$ cycloalkyl, substituted or unsubstituted aryl alkyl, or substituted or unsubstituted heteroaryl alkyl,
    with an effective amount of an enzyme catalyst *Candida antarctica* lipase fraction B whereby the ester functionality of one of the two diastereomers is stereoselectively hydrolyzed.

6. The process of claim 5 wherein the reaction mixture is aqueous and has a pH of from about 3.0 to 7.5.

7. The process of claim 6 wherein the reaction mixture further comprises an organic phase comprising an immiscible organic solvent.

8. The process of claim 5 wherein the reaction mixture comprises a water-miscible organic solvent to which is added an effective amount of water for hydrolysis and enzyme activity.

9. The process of claim 1, further comprising (B) isolating N-(alkoxycarbonyl)-4-keto-D-proline alkyl ester from the reaction mixture;

(C) reducing N-(alkoxycarbonyl)-4-keto-D-proline alkyl ester to produce N-(alkoxycarbonyl)-cis-4-hydroxy-D-proline alkyl ester;

(D) hydrolyzing the alkyl ester and N-(alkoxycarbonyl) groups of the product of step (C) to yield cis-4-hydroxy-D-proline; and (E) recovering the product of step (D).

10. The process of claim 9, wherein the reducing step (C) is by catalytic hydrogenation.

11. A process for separating a racemic mixture of N-(alkoxycarbonyl)-4-keto-D,L-proline alkyl esters comprising (A) contacting in a reaction mixture a racemic mixture of N-(alkoxycarbonyl)-4-keto-D,L-proline alkyl esters of formula I,

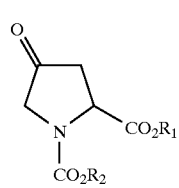

I where
      $R_1$ is selected from the group consisting of unsubstituted or substituted $C_1$–$C_6$ alkyl or alkenyl, and $C_3$–$C_6$ cycloalkyl, and
      $R_2$ is independently selected from the group consisting of unsubstituted or substituted $C_1$–$C_6$ alkyl or alkenyl, $C_3$–$C_6$ cycloalkyl, substituted or unsubstituted aryl alkyl, or substituted or unsubstituted heteroaryl alkyl, with an effective amount of enzyme catalyst *Candida antarctica* lipase fraction B whereby the ester functionality of the corresponding L-enantiomer of the racemic mixture is enantioselectively hydrolyzed;

(B) isolating the unhydrolyzed D-enantiomer from the hydrolyzed L-enantiomer;

(C) reducing the N-(alkoxycarbonyl)-4-keto-D-proline alkyl ester to the corresponding N-(alkoxycarbonyl)-cis-4-hydroxy-D-proline alkyl ester;

(D) hydrolyzing the alkyl ester and N-(alkoxycarbonyl) groups of the product of step (C) whereby cis-4-hydroxy-D-proline is produced; and (E) recovering the product of step (D).

12. A process for separating a mixture of diastereomeric pairs of N-(alkoxycarbonyl)-4-hydroxyproline alkyl esters comprising (A) contacting in a reaction mixture a diastereomeric mixture of N-(alkoxycarbonyl)-4-hydroxyproline alkyl esters of formula II,

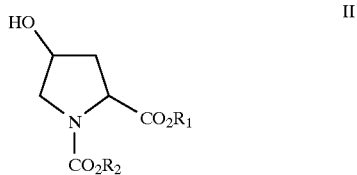

where $R_1$ is selected from the group consisting of unsubstituted or substituted $C_1$–$C_6$ alkyl or alkenyl, and $C_3$–$C_6$ cycloalkyl, and $R_2$ is independently selected from the group consisting of unsubstituted or substituted $C_1$–$C_6$ alkyl or alkenyl, $C_3$–$C_6$ cycloalkyl, substituted or unsubstituted aryl alkyl, or substituted or unsubstituted heteroaryl alkyl, with an effective amount of enzyme catalyst *Candida antarctica* lipase fraction B whereby the ester functionality of one of the two diastereomers is stereoselectively hydrolyzed;

(B) separating the unhydrolyzed N-(alkoxycarbonyl)-4-hydroxyproline alkyl ester from the N-(alkoxycarbonyl)-4-hydroxyproline hydrolysis product; and (C) hydrolyzing the ester and N-(alkoxycarbonyl) groups of the isolated N-(alkoxycarbonyl)-4-hydroxyproline alkyl ester to produce a diastereomer of 4-hydroxyproline.

13. The process of claim 12 wherein in step (A) the diastereomeric mixture of N-(alkoxycarbonyl)-4-hydroxyproline alkyl esters of formula II is comprised of N-(alkoxycarbonyl)-cis-4-hydroxy-L-proline alkyl ester and N-(alkoxycarbonyl)-trans-4-hydroxy-L-proline alkyl ester and the product produced in step (C) is cis-4-hydroxy-L-proline.

14. The process of claim 12 wherein in step (A) the diastereomeric mixture of N-(alkoxycarbonyl)-4-hydroxyproline alkyl esters of formula II is comprised of N-(alkoxycarbonyl)-cis-4-hydroxy-L-proline alkyl ester and N-(alkoxycarbonyl)-trans-4-hydroxy-D-proline alkyl ester and the product produced in step (C) is trans-4-hydroxy-D-proline.

15. The process of claim 12 further comprising (D) hydrolyzing the N-(alkoxycarbonyl) group of the remaining N-(alkoxycarbonyl)-4-hydroxyproline of step (A) to produce a second diastereomer of 4-hydroxyproline.

16. The process of claim 15 wherein in step (A) the diastereomeric mixture of N-(alkoxycarbonyl)-4-hydroxyproline alkyl esters of formula II is comprised of N-(alkoxycarbonyl)-cis-4-hydroxy-D-proline alkyl ester and N-(alkoxycarbonyl)-trans-4-hydroxy-L-proline alkyl ester, the product produced in step (C) is cis-4-hydroxy-D-proline, and the product produced in step (D) is trans-4-hydroxy-L-proline.

17. The process of claim 15 wherein in step (A) the diastereomeric mixture of N-(alkoxycarbonyl)-4-hydroxyproline alkyl esters of formula II is comprised of N-(alkoxycarbonyl)-cis-4-hydroxy-D-proline alkyl ester and N-(alkoxycarbonyl)-cis-4-hydroxy-L-proline alkyl ester, the product produced in step (C) is cis-4-hydroxy-D-proline, and the product recovered in step (D) is cis-4-hydroxy-L-proline.

18. The process of claim 15 wherein in step (A) the diastereomeric mixture of N-(alkoxycarbonyl)-4-hydroxyproline alkyl esters of formula II is comprised of N-(alkoxycarbonyl)-trans-4-hydroxy-D-proline alkyl ester and N-(alkoxycarbonyl)-trans-4-hydroxy-L-proline alkyl ester, the product produced in step (C) is trans-4-hydroxy-D-proline, and the product produced in step (D) is trans-4-hydroxy-L-proline.

19. The process of claims 1, 5, 9 or 15 wherein the enzyme catalyst is in the form of whole microbial cells which express *Candida antarctica* lipase fraction B.

20. The process of claims 1, 5, 9 or 15 wherein the enzyme catalyst *Candida antarctica* lipase fraction B is immobilized on an insoluble inorganic carrier, or on a soluble or insoluble organic carrier.

* * * * *